United States Patent [19]

Gadea

[11] 4,126,443

[45] Nov. 21, 1978

[54] INHIBITION OF CRYSTAL FORMATION OF 1,2-DIMETHYL-3,5-DIPHENYL-PYRAZOLIUM METHYL SULFATE IN AQUEOUS SOLUTIONS WITH AN ACRYLAMIDE POLYMER

[75] Inventor: Ramon A. Gadea, Lawrenceville, N.J.

[73] Assignee: American Cyanamid Company, Stamford, Conn.

[21] Appl. No.: 853,711

[22] Filed: Nov. 21, 1977

[51] Int. Cl.$^2$ .................... A01N 17/08; A01N 9/22; C07D 231/12
[52] U.S. Cl. ................... 71/92; 71/DIG. 1; 548/373
[58] Field of Search ............. 71/92, DIG. 1; 548/373

[56] References Cited

FOREIGN PATENT DOCUMENTS 4,810,535 4/1969 Japan.

OTHER PUBLICATIONS

British Pat. 1,056,887, Chem. Abst. vol. 66 (1967) 94152p.

*Primary Examiner*—Catherine L. Mills
*Attorney, Agent, or Firm*—Harry H. Kline

[57] ABSTRACT

The present invention relates to a liquid composition comprising a water soluble acrylamide polymer, 1,2-dimethyl-3,5-diphenylpyrazolium methyl sulfate, a surfactant and water. More particularly, this invention relates to the use of a water soluble hydrolyzed acrylamide polymer for the inhibition of partial recrystallization of 1,2-dimethyl-3,5-diphenylpyrazolium methyl sulfate from aqueous solutions thereof.

7 Claims, No Drawings

INHIBITION OF CRYSTAL FORMATION OF 1,2-DIMETHYL-3,5-DIPHENYLPYRAZOLIUM METHYL SULFATE IN AQUEOUS SOLUTIONS WITH AN ACRYLAMIDE POLYMER

The herbicidal compound: 1,2-dimenthyl-3,5-diphenylpyrazolium methyl sulfate is disclosed in U.S. Pat. No. 3,882,142, issued May 6, 1975 to B. L. Walworth et al., incorporated herein by reference. The method of use of the above-identified herbicide for the postemergence control of undesirable weeds, especially wild oats (Avena fatua) in the presence of barley and wheat is disclosed in U.S. Pat. No. 3,992,161, issued Nov. 25, 1975 to B. L. Walworth et al., also incorporated herein by reference.

Due to excellent solubility in water, the above herbicide is preferably formulated and sold to the ultimate user as an aqueous concentrate.

It has been found, however, that such aqueous compositions, when stored and/or kept at temperatures of 5° C. or lower, deposit crystals of said herbicide, and thereby lower the concentration of said herbicidal component.

Although an aqueous composition containing crystals of 1,2-dimethyl-3,5-diphenylpyrazolium methyl sulfate can be restored to its original strength by heating and agitating same, obviously it would be of advantage to all concerned to prepare liquid compositions from which said herbicide would not crystallize out at or below 5° C.

The herbicidal compound utilized in the novel compositions of the present invention: 1,2-dimethyl-3,5-diphenylpyrazolium methyl sulfate of formula:

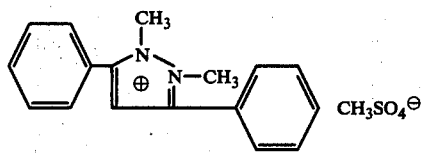

is very effective for the postemergence control of wild oats (Avena fatua) in the presence of barley and wheat.

Due to its excellent solubility in water, the above herbicide is marketed preferably as an aqueous composition comprising from about 20% to 40% by weight of said herbicide, from about 9% to 13% by weight of a surfactant such as octylphenoxy polyethoxy ethanol and the like, while the balance of the composition is water.

The resultant compositions containing said herbicide are quite stable, except, when stored, shipped and/or kept at temperatures of 5° C. or lower. Under these conditions the compositions deposit in crystalline form a significant fraction of the aforesaid 1,2-dimethyl-3,5-diphenylpyrazolium methyl sulfate, which then settles to the bottom of the container. Although the thus formed crystalline precipitate can be redissolved and the aqueous composition reconstituted to its original strength by heating and stirring said crystal containing composition, it is cumbersome and time consuming to do so.

The seriousness of the above described partial crystallization of said herbicide from the aqueous composition can not be underestimated, considering, that these compositions are usually manufactured during Winter in preparation for early Spring use, and thus the bulk of the manufactured product may be shipped to the distributors in unheated freight cars and stored in unheated warehourses.

These liquid compositions, even though they may have been manufactured in the Spring or early Summer, still may be exposed to subzero temperatures, while in transit through high alpine regions, and thus would arrive at their destination with part of the 1,2-dimethyl-3,5-diphenylpyrazolium methyl sulfate having been crystallized out of solution in transit.

Surprisingly, we now find that partial recrystallization and precipitation of the crystals of 1,2-dimethyl-3,5-diphenylpyrazolium methyl sulfate from said aqueous compositions at temperatures below 5° C. can be effectively inhibited by incorporating into said compositions a small amount of a water soluble hydrolyzed acrylamide polymer.

The acrylamide polymer used herein is a hydrolyzed polyacrylamide having from 1 to 50% unhydrolyzed amide groups and having an average molecular weight from 500 to 25000. Preferably the polymer has from 10–20% unhydrolyzed amide groups and a molecular weight of 1000 to 10,000.

Advantageously, aqueous compositions containing said crystallization inhibitor acrylamide polymer may be prepared as follows: 20% to 40% by weight of 1,2-dimethyl-3,5-diphenylpyrazolium methyl sulfate, 9% to 13% by weight of octylphenoxy-polyethoxy ethanol and from about 20 ppm to 640 ppm by weight and preferably 160 ppm to 640 ppm by weight of the acrylamide polymer, are dissolved in water, with slight warming if necessary. The thus obtained solution may be adjusted to 100% by the addition of water.

Thus we find that inclusion of at least 20 ppm by weight of the acrylamide polymer in the composition of the present invention will inhibit crystallization of said herbicide from the composition to a low temperature of +1.7° C. Increasing the amount of said acrylamide polymer in said herbicidal composition to at least 60 ppm by weight inhibits the crystallization of 1,2-dimethyl-3,5-diphenylpyrazolium methyl sulfate to a low temperature of −1.7° C. Depending on the percent by weight of 1,2-dimethyl-3,5-diphenylpyrazolium methyl sulfate present in said aqueous compositions, inclusion of from 160 ppm to 640 ppm by weight of acrylamide polymer of the above definition, or 320 ppm to 640 ppm by weight of said polymer will inhibit the crystallization of said herbicide from the compositions to a low temperature of −5° C. or −7.5° C., respectively.

A typical aqueous composition of the present invention, inhibited from partial crystallization of the herbicide to a low temperature of −5° C. comprises 32.1% by weight (real) of 1,2-dimethyl-3,5-diphenylpyrazolium methyl sulfate, 12.3% by weight of octylphenoxy-polyethoxy ethanol, 480 ppm to 640 ppm by weight of an acrylamide polymer (of an average molecular weight of 8,000 and 15% unhydrolyzed amide groups), wherein the balance of the composition is water.

Another typical composition of the present invention, inhibited from partial crystallization of the herbicide to a low temperature of −7.5° C., comprises 27.5% by weight (real) of 1,2-dimethyl-3,5-diphenylpyrazolium methyl sulfate, 9.33% by weight of octylphenoxy-polyethoxy ethanol, 320 ppm to 640 ppm by weight of the above-defined acrylamide polymer, wherein the balance of the composition is water.

The aqueous compositions are diluted with water to the concentration desired to deliver the herbicide at the kg/ha rates selected. Application of the dilute aqueous sprays can be executed with commercially available spraying equipment.

The dilute aqueous sprays prepared from the compositions of the present invention, containing the acrylamide polymer crystallization inhibitor are highly effective for the control of wild oats in the presence of barley and wheat.

This invention is further illustrated by the non-limiting examples set forth below.

EXAMPLE 1

General procedure for the preparation of the novel compositions of the present invention containing an acrylamide polymer as a crystallization inhibitor One hundred to 400 grams samples of said compositions are prepared by dissolving 1,2-dimethyl-3,5-diphenylpyrazolium methyl sulfate and octylphenoxy polyethoxy ethanol surfactant in a minimum amount of water. Next, the acrylamide polymer (Av. mol. wt. 8,000 with 15% unhydrolyzed amide groups) is added as a 1% aqueous solution in the amounts (ppm) designated. Water is added to the thus obtained solution in sufficient quantity to adjust the weight of the solution to 100%. By the above procedure, compositions, representative of commercial formulations are prepared, containing varying amounts of acrylamide polymer, as shown in Table I below.

Table 1

Aqueous Compositions Containing 1,2-dimethyl-3,5-diphenylpyrazolium Methyl Sulfate and an Acrylamide Polymer as Crystallization Inhibitor

| Component | Percent by Weight | |
|---|---|---|
| | Formula A | Formula B |
| 1,2-Dimethyl-3,5-diphenylpyrazolium methyl sulfate (real) | 32.1 | 27.5 |
| Octylphenoxy polyethoxy ethanol (surfactant) | 12.3 | 9.33 |
| Acrylamide polymer in ppm | 0–1000 | 0–5353 |
| Water q.s. ad | 100.00 | 100.00 |

EXAMPLE 2

Evaluation of the efficacy of a water soluble acrylamide polymer as crystallization inhibitor for 1,2-dimethyl-3,5-diphenylpyrazolium methyl sulfate in solutions thereof The unfiltered liquid compositions prepared by the procedures of Example 1 are divided into 1-oz narrow mouth bottles as required for several temperature levels. All samples are cooled to 5° C. and then inoculated with seed crystals of the above herbicide (seed crystal size: 30–50 mesh). The thus seeded samples are kept at least for one week at 5° C. If during this time the seed crystals dissolve, the samples are cooled to 1.7° C., reseeded and are kept at least one week at 1.7° C.

For below freezing (0° C.) temperature, the samples are transferred to 20 ml injection vials, cooled to 1.7° C., inoculated with seed crystals, then the vials are capped with rubber septa and sealed with aluminum caps. The thus prepared samples are then cooled to −1.7° C., −5° C. or −7.5° C., respectively, by total immersion in a cold bath of corresponding temperature and stored at least for one week at these temperatures.

When ready for sampling, the bottles and vials are shaken cold, allowed to settle (at their respective temperatures) and samples of the clear solutions are then removed for analyses, with a pipette from the bottles and with a syringe from the vials. The samples are assayed with a spectrophotometer by UV absorption at about 380 nanometers.

Tables II and III below show the effect of the concentration of the acrylamide polymer on the percent of the 1,2-dimethyl-3,5-diphenylpyrazolium methyl sulfate remaining in solution at the specified temperatures. The increase in the amount of the sulfate compound beyond that in the original solutions is due to the seed crystals.

TABLE II

Evaluation of the Efficacy of Acrylamide Polymer in Aqueous Compositions Containing 32.1% by Weight of 1,2-Dimethyl-3,5-Dimethylpyrazolium Methyl Sulfate

| Acrylamide Polymer, ppm | % of Sulfate Compound Remaining in Solution |
|---|---|
| 5° C. | |
| 160 | 31.6 |
| 0 | 28.7 |
| 1.7° C. | |
| 750 | 20.4 |
| 640 | 20.0 |
| 500 | 20.9 |
| 480 | 32.6 |
| 320 | 32.8 |
| 160 | 32.0 |
| 0 | 19.3–23.8 |
| −1.7° C. | |
| 1000 | 22.3 |
| 750 | 17.3 |
| 640 | 16.8 |
| 500 | 17.2 |
| 480 | 32.9 |
| 420 | 32.9 |
| 320 | 32.9 |
| 250 | 33.1 |
| 160 | 23.8 |
| 0 | 17.7 |
| −5° C. | |
| 1000 | 23.7 |
| 750 | 16.0 |
| 640 | 15.7 |
| 500 | 15.3 |
| 480 | 30.7 |
| 400 | 27.8 |
| 320 | 27.5 |
| 240 | 25.5 |
| 160 | 26.2 |
| 0 | 14.3 |

TABLE III

Evaluation of the Efficacy of Acrylamide Polymer in Aqueous Compositions Containing 27.5% by Weight of 1,2-Dimethyl-3,5-Diphenylpyrazolium Methyl Sulfate

| Acrylamide Polymer, ppm | % of Sulfate Compound Remaining in Solution |
|---|---|
| −5° C. | |
| 5353 | 13.2 |
| 1862 | 14.9 |
| 640 | 26.6 |
| 340 | 26.6 |
| 170 | 27.4 |
| 140 | 24.7 |
| 100 | 25.9 |
| 80 | 21.9 |
| 65 | 22.3 |
| 50 | 18.5 |
| 40 | 18.9 |
| 20 | 18.0 |
| 15 | 16.5 |
| 0 | 14.7 |

What is claimed is:

1. An aqueous composition comprising (a) an herbicidally effective amount from about 20% to about 40% by weight, of 1,2-dimethyl-3,5-diphenylpyrazolium methyl sulfate, (b) from about 9% to about 13%, by weight, of octyl phenoxy polyethoxy ethanol, (c) from about 20 ppm to about 640 ppm, by weight, of a hydrolyzed acrylamide polymer having an average molecular weight of 7000 to 9000 and from about 10% to about 20% unhydrolyzed amide groups, and (d) the balance being water, whereby said acrylamide polymer inhibits both the partial crystallization and precipitation of said pyrazolium salt from said liquid composition at temperatures ranging from +5° C. to −7.5° C.

2. A composition according to claim 1, wherein the amount of said acrylamide polymer is 160 to 320 parts per million.

3. A composition according to claim 1, wherein the amount of said acrylamide polymer is 320 to 640 parts per million.

4. A composition according to claim 1, comprising 160 to 640 parts per million of acrylamide polymer, 27.5% by weight of 1,2-dimethyl-3,5-diphenylpyrazolium methyl sulfate and 9.33% by weight of octylphenoxy polyethoxy ethanol.

5. A composition according to claim 1, comprising 160 to 640 parts per million of acrylamide polymer, 32.1% by weight of 1,2-dimethyl-3,5-diphenylpyrazolium methyl sulfate and 12.3% by weight of octylphenoxy polyethoxy ethanol.

6. A method for the inhibition of formation and growth of crystals of 1,2-dimethyl-3,5-diphenylpyrazolium methyl sulfate in aqueous solutions thereof, comprising adding to said solutions a hydrolyzed acrylamide polymer of an average molecular weight of about 7000 to 9000 and about 10 to 20% unhydrolyzed amide groups in amounts effective to inhibit the formation and growth of crystals of said 1,2-dimethyl-3,5-diphenylpyrazolium methyl sulfate.

7. A method according to claim 6, wherein said acrylamide polymer is added in amounts from 20 to 640 parts per million to said aqueous solution of 1,2-dimethyl-3,5-diphenylpyrazolium methyl sulfate.

* * * * *